US00PP17639P2

(12) United States Plant Patent
Verschoor

(10) Patent No.: US PP17,639 P2
(45) Date of Patent: Apr. 24, 2007

(54) ***VERONICA* PLANT NAMED 'PURPLEICIOUS'**

(50) Latin Name: *Veronica hybrida*
Varietal Denomination: Purpleicious

(75) Inventor: Jan Verschoor, Haarlem (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/273,530

(22) Filed: Nov. 14, 2005

(51) Int. Cl.
*A01H 5/00* (2006.01)

(52) U.S. Cl. ..... Plt./251

(58) Field of Classification Search ..... Plt./251
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Veronica* plant named 'Purpleicious', characterized by its upright, compact and sturdy plant habit; freely basal branching habit; dense and bushy plant form; long flower racemes; freely flowering habit; and purple violet-colored flowers.

2 Drawing Sheets

Botanical designation: *Veronica hybrida.*
Cultivar denomination: 'Purpleicious'.

BACKGROUND OF THE INVENTION

The present Invention relates to a new and distinct cultivar of *Veronica* plant, botanically known as *Veronica hybrida,* and hereinafter referred to by the cultivar name 'Purpleicious'.

The new *Veronica* is a product of a planned breeding program conducted by the Inventor in Haarlem, The Netherlands. The objective of the breeding program was to create sturdy new *Veronica* cultivars with numerous flowers with attractive coloration.

The new *Veronica* originated from a cross-pollination made by the Inventor in July, 1998 of a proprietary *Veronica longifolia*×*Veronica spicata* selection, not patented, as the female, or seed, parent with a proprietary *Veronica spicata*× *Veronica longifolia* selection, not patented, as the male, or pollen, parent. The new *Veronica* was discovered and selected by the Inventor during the summer of 2000 as a single flowering plant within the progeny of the stated cross-pollination in a controlled environment in Haarlem, The Netherlands.

Asexual reproduction of the new cultivar by cuttings since 2001 in Haarlem, The Netherlands, has shown that the unique features of this new *Veronica* are stable and reproduced true to type in successive generations.

SUMMARY OF THE INVENTION

Plants of the cultivar Purpleicious have not been observed under all possible environmental conditions. The phenotype may vary somewhat with variations in environment such as temperature and light intensity without, however, any variance in genotype.

The following traits have been repeatedly observed and are determined to be the unique characteristics of 'Purpleicious'. These characteristics in combination distinguish 'Purpleicious' as a new and distinct *Veronica* cultivar:

1. Upright, compact and sturdy plant habit.
2. Freely basal branching habit, dense and bushy plant form.
3. Long flower racemes.
4. Freely flowering habit.
5. Purple violet-colored flowers.

Plants of the new *Veronica* can be compared to the parent selections. Compared to plants of the parent selections, plants of the new *Veronica* are more compact, are sturdier, have shorter flower racemes and have more distinct flower coloration.

Plants of the new *Veronica* can be compared to plants of the *Veronica* cultivar Sunny Border Blue, not patented. Plants of the new *Veronica* differ from plants of the cultivar Sunny Border Blue in the following characteristics:

1. Plants of the new *Veronica* are more compact and sturdier than plants of the cultivar Sunny Border Blue.
2. Plants of the new *Veronica* have longer flower racemes than plants of the cultivar Sunny Border Blue.
3. Plants of the new *Veronica* have purple violet-colored flowers whereas plants of the cultivar Sunny Border Blue have blue violet-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica.*

The photograph on the first sheet comprises a side perspective view of typical flowering plants of 'Purpleicious' grown in an outdoor nursery.

The photograph at the top of the second sheet is a side perspective view of a typical vegetative plant of 'Purpleicious'.

The photograph at the bottom of the second sheet is a close-up view of a typical leaf of 'Purpleicious'.

DETAILED BOTANICAL DESCRIPTION

Plants shown in the aforementioned photographs and used in the following description were grown under conditions which closely approximate commercial production conditions during the summer in an outdoor nursery in Lisse, The Netherlands. During the production of the plants, day temperatures ranged from 10° C. to 30° C. and night temperatures ranged from 4° C. to 15° C. Plants were about two years old when the photographs and description were taken. In the following description, color references are made to The Royal Horticultural Society Colour Chart, 2001 Edition, except where general terms of ordinary dictionary significance are used.

Botanical classification: *Veronica hybrida* cultivar Purpleicious.

Parentage:

*Female, or seed, parent.*—Proprietary *Veronica longifolia*×*Veronica spicata* selection, not patented.

*Male, or pollen, parent.*—Proprietary *Veronica spicata*×*Veronica longifolia* selection, not patented.

Propagation:

*Type.*—By cuttings.

*Time to produce a rooted young plant.*—About one month during the spring.

*Root description.*—Thick; freely branching.

Plant description:

*Form.*—Perennial. Upright, compact and sturdy plant habit; inverted triangle. Freely basal branching with about 26 flowering stems per plant; dense and bushy plant habit; moderately vigorous growth habit. Numerous flowers arranged on crowded terminal racemes.

*Plant height.*—About 44 cm.

*Plant width.*—About 33 cm.

*Lateral stem description.*—Length (excluding inflorescence): About 23.2 cm. Diameter: About 3 mm. Internode length: About 2.3 cm. Strength: Strong. Texture: Sparsely pubescent. Color: 144A.

*Foliage description.*—Arrangement: Opposite, simple. Length: About 9.4 cm. Width: About 2.7 mm. Shape: Lanceolate. Apex: Acute. Base: Attenuate. Margin: Serrate. Texture, upper and lower surfaces: Smooth, glabrous. Venation pattern: Pinnate. Color: Developing foliage, upper surface: Darker than 144A. Developing foliage, lower surface: 137C. Fully expanded foliage, upper surface: 137A to 139A. Fully expanded foliage, lower surface: 138B to 138C. Venation, upper and lower surfaces: 144A to 144B. Petiole length: About 2 cm. Petiole diameter: About 4 mm. Petiole color: 144A to 144B.

Flower description:

*Flower arrangement and shape.*—Single campanulate flowers closely spaced on upright terminal racemes; flowers face mostly outward. Freely flowering habit, about 300 flowers per raceme.

*Natural flowering season.*—Continuous flowering from July to late September in The Netherlands.

*Flower longevity on the plant.*—Individual flowers last about one week on the plant. Flowers not persistent.

*Fragrance.*—None detected.

*Flower buds.*—Length: About 4 mm. Diameter: About 2 mm. Shape: Ovoid. Color: N81A.

*Inflorescence size.*—Length: About 20.8 cm. Diameter: About 2.1 cm.

*Flowers.*—Diameter: About 6 mm. Depth (height): About 8 mm.

*Petals.*—Arrangement: Campanulate; four petals fused towards the base. Length: About 5 mm. Width: About 2.5 mm. Shape: Oblanceolate. Apex: Broadly acute. Margin: Entire. Texture: Smooth, glabrous. Color: When opening, upper and lower surfaces: N81B. Fully opened, upper and lower surfaces: N81B.

*Sepals.*—Arrangement: Four sepals fused towards the base; lower two sepals nearly twice as long as upper two sepals. Length, upper sepals: About 3 mm. Length, lower sepals: About 5.5 mm. Width, upper sepals: About 1 mm. Width, lower sepals: About 1.5 mm. Shape: Lanceolate. Apex: Acute. Base: Cuneate, fused. Margin: Entire. Texture, upper and lower surfaces: Smooth, glabrous. Color, upper surface: 137A to 137B. Color, lower surface: 137C.

*Peduncles.*—Length: About 20.8 cm. Diameter: About 1.5 mm. Aspect: Erect to 30° from vertical. Strength: Strong. Color: 143A to 143B.

*Pedicels.*—Length: About 2 mm. Diameter: About 0.5 mm. Aspect: About 55° from vertical. Strength: Strong. Color: 143A to 143B.

*Reproductive organs.*—Stamens: Quantity per flower: Two. Filament length: About 6 mm. Filament color: N80C. Anther shape: Elliptic. Anther length: About 1 mm. Anther color: N74B. Pollen amount: Scarce. Pollen color: 4D. Pistils: Quantity per flower: One. Pistil length: About 6 mm. Stigma shape: Clavate, flattened. Stigma color: N80B. Style length: About 5 mm. Style color: N81B. Ovary color: N81B. Fruit: Length: About 3 mm. Diameter: About 3 mm. Texture: Smooth. Color: 144A to 144B. Seed: Quantity per fruit: About 20. Length: About 1 mm. Diameter: About 1 mm. Texture: Smooth. Color: N199C to N199D.

Disease/pest resistance: Plants of the new *Veronica* have not been noted to be resistant to pathogens and pests common to *Veronica*.

High temperature tolerance: Plants of the new *Veronica* have been observed to tolerate temperatures up to 30° C.

Hardiness: Plants of the new *Veronica* have been observed to be hardy to USDA Zone 4.

It is claimed:

1. A new and distinct cultivar of *Veronica* plant named 'Purpleicious', as illustrated and described.

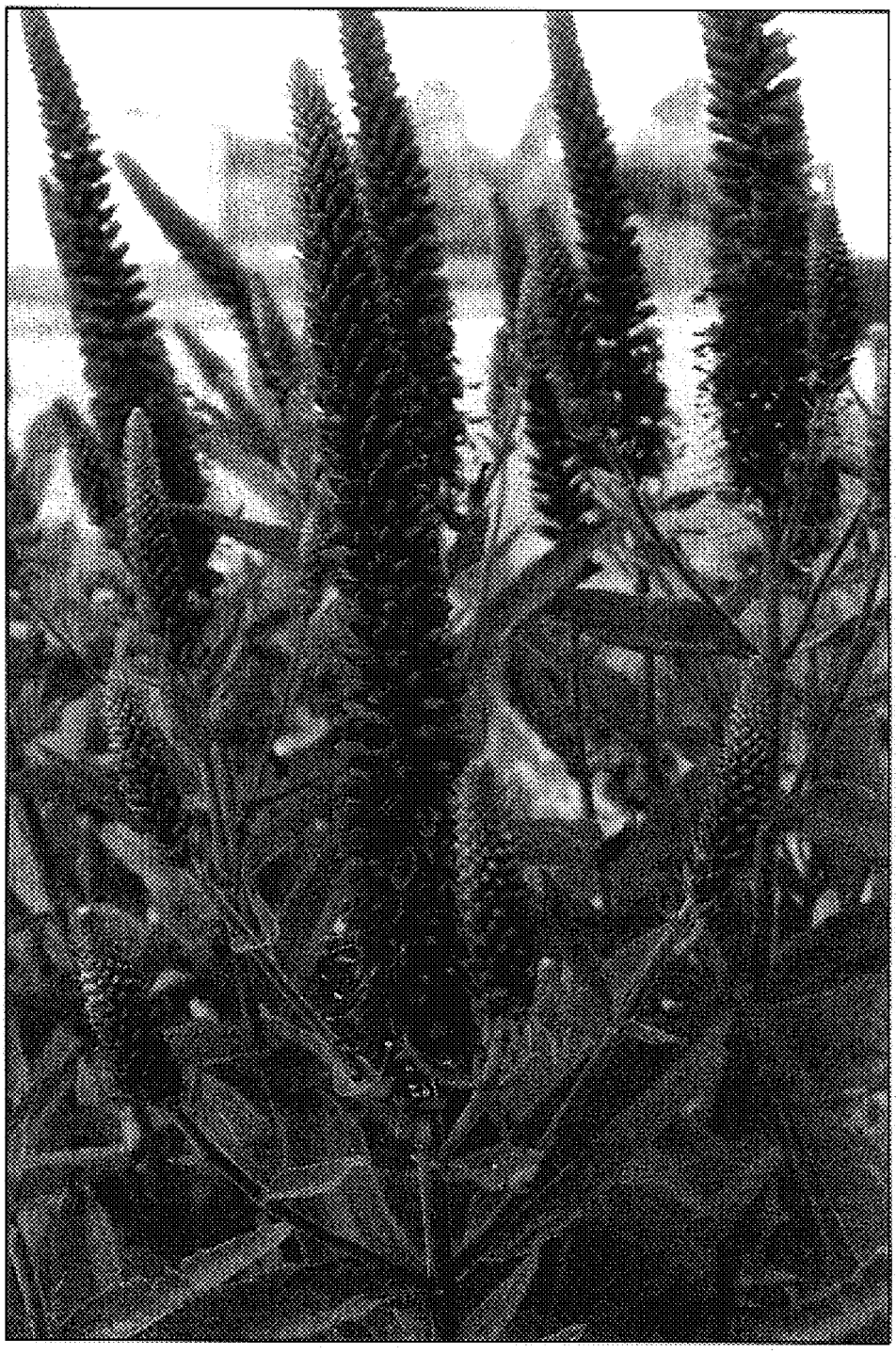

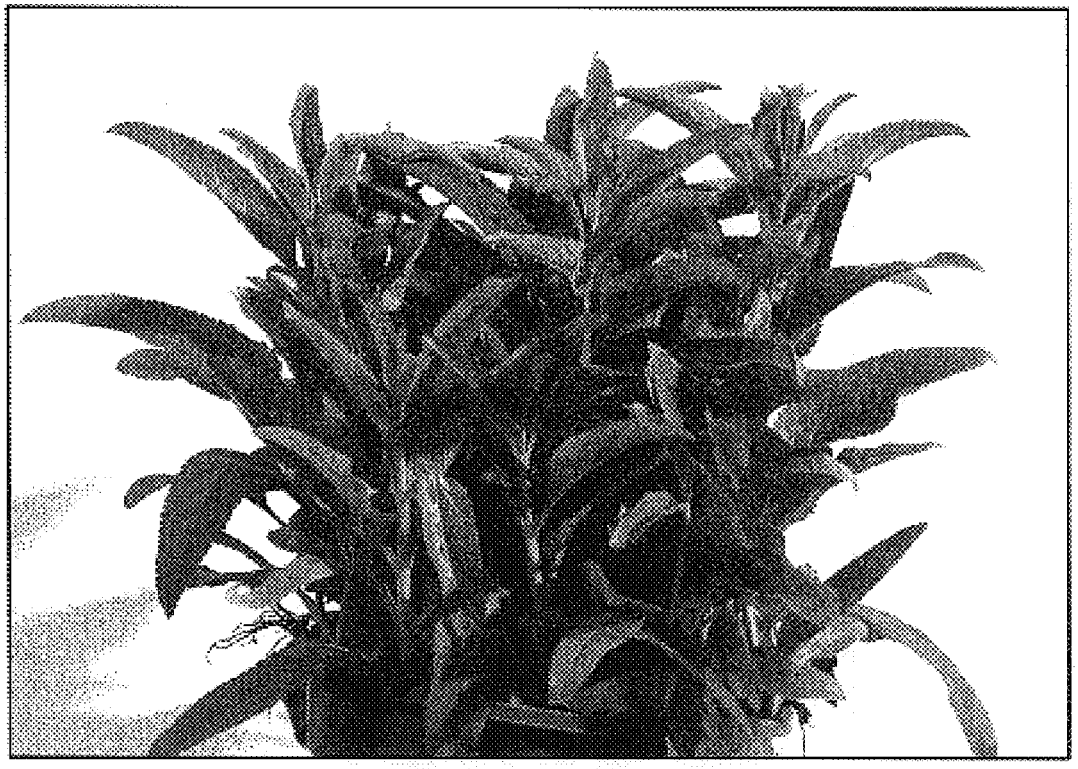
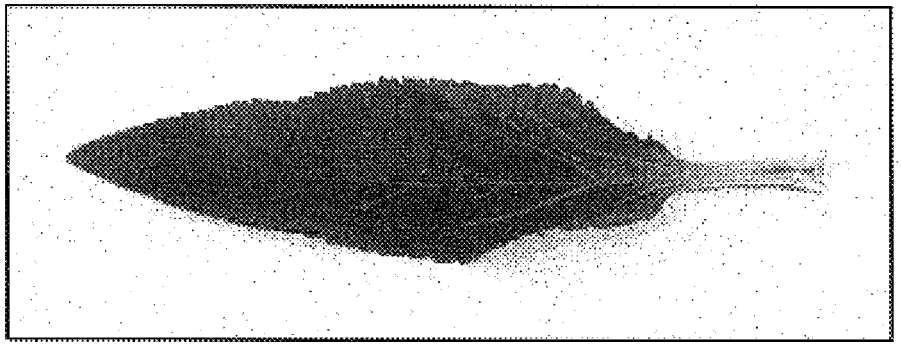

* * * * *